United States Patent [19]

Toyomaki

[11] 4,364,947
[45] Dec. 21, 1982

[54] VINCAMINE DERIVATIVES USEFUL AS CEREBRAL METABOLIC AND CIRCULATORY REGULATORS

[75] Inventor: Yoshio Toyomaki, Nara, Japan

[73] Assignee: Nippon Zoki Pharmaceutical Co., Ltd., Osaka, Japan

[21] Appl. No.: 261,977

[22] Filed: May 8, 1981

[30] Foreign Application Priority Data

May 16, 1980 [JP] Japan .................... 55-65774

[51] Int. Cl.$^3$ .................. A61K 31/435; C07D 461/00
[52] U.S. Cl. ........................ 424/256; 546/51
[58] Field of Search ................ 546/51; 424/256

[56] References Cited

U.S. PATENT DOCUMENTS 4,123,535  10/1978  Pfaffli ................. 424/256

FOREIGN PATENT DOCUMENTS 2253502  8/1975  France ................. 546/51
1405127  9/1975  United Kingdom .
1445956  8/1976  United Kingdom .
1518987  7/1978  United Kingdom .

OTHER PUBLICATIONS

Yamada, et al., Chemical Abstracts, vol. 82, 15735k (1975).

*Primary Examiner*—Donald G. Daus
*Assistant Examiner*—Diana G. Rivers
*Attorney, Agent, or Firm*—Pennie & Edmonds

[57] ABSTRACT

This invention relates to novel vincamine derivatives useful as cerebral metabolic and circulatory regulators. The compounds have the following structural formula:

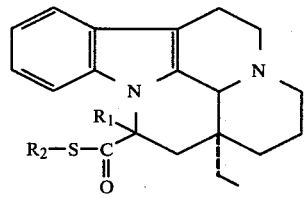

wherein $R_1$ is hydrogen or a hydroxyl group and $R_2$ is an alkyl group.

9 Claims, 2 Drawing Figures

VINCAMINE DERIVATIVES USEFUL AS CEREBRAL METABOLIC AND CIRCULATORY REGULATORS

TECHNICAL FIELD

This invention discloses novel vincamine derivatives to be used as cerebral metabolic and circulatory regulators.

The compounds have the following structural formula:

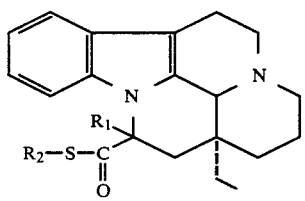

(I)

wherein $R_1$ is hydrogen or a hydroxyl group and $R_2$ is an alkyl group.

BACKGROUND OF THE INVENTION

Vincamine, one of the alkaloids from vinca minor L., is known to have vasodilative effects in the cerebral vessels. Many known derivatives of vincamine have been synthesized. The general structure of vincamine and vincaminic acid are as follows:

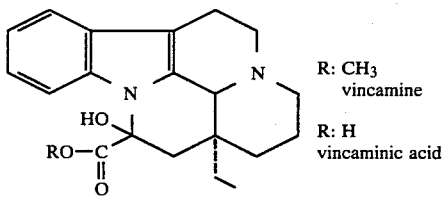

R: CH$_3$ vincamine
R: H vincaminic acid

When vincamine is administered to humans orally, intravenously or intramuscularly, it is hydrolyzed, mainly by liver esterase, to vincaminic acid which lacks activity and is excreted in the urine. The known derivatives of vincamine are alcohol esters of vincaminic acid which are readily hydrolyzed by liver esterase.

SUMMARY OF THE INVENTION

This invention relates to novel vincamine derivatives and their pharmacologically acceptable salts which demonstrate regulating effects on blood circulation and metabolic pathways in the brain.

The present inventor has made every effort to obtain vincamine derivatives which are not easily inactivated in vivo and are therefore, expected to retain the pharmacological effects of vincamine. Subsequently, discovering that new vincaminic acid thioesters demonstrate similar or superior activity to vincamine and are hardly hydrolyzed by liver esterase, the present invention has accomplished the subject invention.

The objects of the present invention are to provide thioesters of vincaminic acid or deoxyvincaminic acid and their pharmacologically acceptable salts for use as cerebral metabolic and circulatory regulators demonstrating a prolonged retaining effect, a process for producing them and pharmaceutical compositions containing the present compound as an active ingredient.

DETAILED DESCRIPTION OF THE INVENTION

Figure 1:
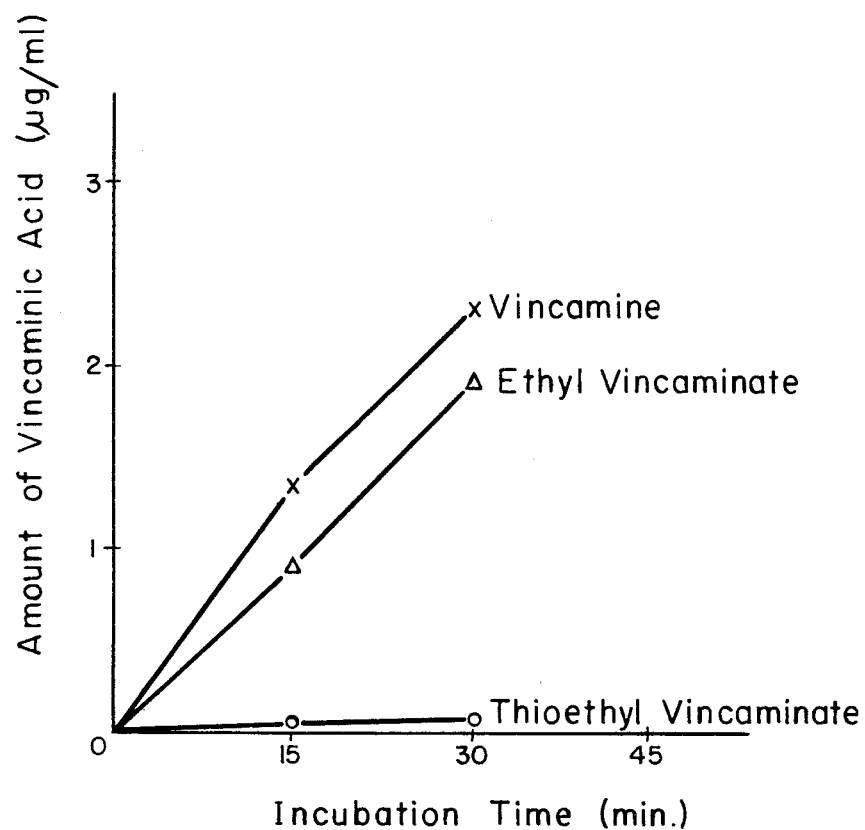
FIG. 1 is a graph showing relative rates of hydrolysis of the thioethyl vincaminate compound of the present invention and comparative compounds using guinea pig liver homogenate.

The compounds according to the present invention are novel thioesters of the following general formula (I);

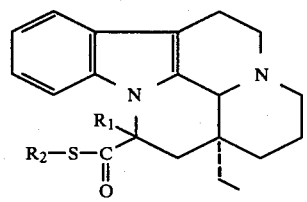

(I)

wherein $R_1$ is hydrogen or a hydroxyl group, and $R_2$ is an alkyl group.

$R_2$ may represent a linear or branched alkyl group, and particularly an alkyl group having one to four carbon atoms. Methyl, ethyl, propyl, isopropyl, butyl, isobutyl, sec-butyl and tert-butyl groups are preferable.

The compounds according to the present invention include each position No. 14 optically active substance and mixtures of both epimers.

This invention also includes pharmacologically acceptable salts of the compound (I). Such salts are acid-addition salts with inorganic or organic acid, such as hydrochloric acid, hydrobromic acid, sulfuric acid, phosphoric acid, formic acid, acetic acid, citric acid, tartaric acid, lactic acid, glycolic acid, malic acid, malonic acid, maleic acid, gluconic acid, succinic acid, stearic acid, ascorbic acid, phthalic acid, benzoic acid, nicotinic acid, salicylic acid, sulfosalicylic acid, palmitic acid, mandelic acid, methanesulfonic acid, benzenesulfonic acid, p-toluenesulfonic acid, 2-hydroxy-3-naphthoic acid, and the like, or tertiary salts with halides such as chloride, bromide or iodide of methyl, ethyl, propyl, butyl, benzyl etc.

The compounds according to the present invention are produced by reacting vincaminic acid or deoxyvincaminic acid of the general formula (II), or its epimer or a mixture thereof,

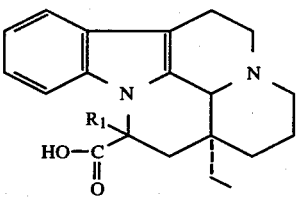

(II)

wherein $R_1$ is hydrogen or a hydroxyl group, with an alkanethiol of the general formula (III);

$R_2$—SH          (III)

wherein $R_2$ is an alkyl group.

The above reaction may be carried out in the presence of a base, such as triethylamine, pyridine, with, preferably, an added synthetic reagent such as, diphenylphosphorylazide.

In this reaction, an inactive solvent such as dimethylformamide, acetone, tetrahydrofuran, dioxane, dimethyl sulfoxide, or chloroform can be used. Cooled condition or mild condition of room temperature may be preferable.

The process for producing the compounds according to the present invention is thioesterification of carboxylic acid of the above formula (II) and, therefore, also includes esterification of reactive derivatives of said carboxylic acid, such as halides, with thiols.

After the reaction, by standard means such as extraction, chromatography, recrystallization and/or reprecipitation, the disclosed compound can be isolated and purified. Furthermore, if desired, conversion to an acid-addition salt or a quaternary salt thereof can be carried out by known methods.

EXAMPLES

The following examples illustrate processes for producing compounds of the present invention and are not to be construed as limiting the scope of the invention in any manner.

EXAMPLE 1

In a liquid mixture of 250 ml of dimethylformamide, 2.5 ml of triethylamine and 2.53 ml of diphenylphosphorylazide, 2 g of vincaminic acid was suspended and 7.2 ml of ethanethiol was dropped. The mixture was reacted at about 20° C. for 24 hours. After the unreacted vincaminic acid was filtered off, water was added to the filtrate and the mixture was left standing overnight. White precipitate thus generated was filtered and dissolved in chloroform. This was washed with water and dried on anhydrous sodium sulfate. The solvent was distilled off under reduced pressure for column chromatography using silica gel. After elution with chloroform and concentration of the fractions of the desired compound for drying, vincaminic acid thioethyl ester was obtained as a colorless granular crystalline through recrystallization from ethanol.

m.p.; 203°–203.5° C. (Dec.)

I R; absorption attributed to thioester at 1685 cm$^{-1}$

|  | C % | H % | N % | S % |
|---|---|---|---|---|
| Calculated | 68.72 | 7.34 | 7.28 | 8.34 |
| Found | 68.80 | 7.50 | 7.11 | 8.32 |

EXAMPLE 2

1.0 g of deoxyvincaminic acid, 1.2 ml of diphenylphosphorylazide, 2.0 ml of ethanethiol and 1.2 ml of triethylamine were added to 30 ml of dimethylformamide under cooling with ice. The mixture was stirred for 3 hours at room temperature, and the reaction was continued until the absence of remaining reactant was confirmed by thin layer chromatography. After an addition of cold water followed by standing, the white suspended product thus generated was filtered and washed with water. This was dissolved in chloroform, washed with a saturated aqueous solution of sodium chloride and dried on anhydrous sodium sulfate. Thereafter, in the same manner as described in Example 1, deoxyvincaminic acid thioethyl ester was obtained in the form of a colorless needle crystalline.

m.p.; 140°–141° C. (Dec)

I R; absorption attributed to thio-ester at 1675 cm$^{-1}$

|  | C % | H % | N % | S % |
|---|---|---|---|---|
| Calculated | 71.70 | 7.66 | 7.60 | 8.70 |
| Found | 71.40 | 7.63 | 7.50 | 8.91 |

The pharmacological tests of the compounds according to the present invention are shown below.

(1) Anti-hypobaric hypoxia test

To ddy-strain male mice 5 mg/Kg of the compounds of the present invention or the comparative compounds were administered intravenously at the tail. After ten minutes, the mice were placed in a vacuum desiccator containing at the bottom a petri dish with a saturated aqueous solution of potassium hydroxide immersing a thimble. The pressure of the desiccator was reduced to 180 mmHg. Thereafter, their survival time was measured at every five seconds. The test was run twenty times. Average time ± standard error was determined, regarding as 600 seconds the case of survival time over 10 minutes. The results are shown below.

| Tested compounds | Survival time (sec.) |
|---|---|
| control | 98.0 ± 14.6 |
| vincamine | 149.0 ± 29.6 |
| vincaminic acid ethyl ester | 114.5 ± 18.4 |
| vincaminic acid thioethyl ester | 139.3 ± 20.4 |

According to the method detailed above, the results are shown below in the case of a 15 mg/Kg intraperitoneal administration.

| Tested compounds | Survival time (sec.) |
|---|---|
| control | 75.8 ± 6.95 |
| vincamine | 270.0 ± 57.96 |
| deoxyvincaminic acid thioethyl ester | 350.8 ± 71.78 |
| pentoxifylline (75 mg/Kg) | 80.8 ± 6.50 |

(2) Hydrolysis by liver homogenate

Figure 2:
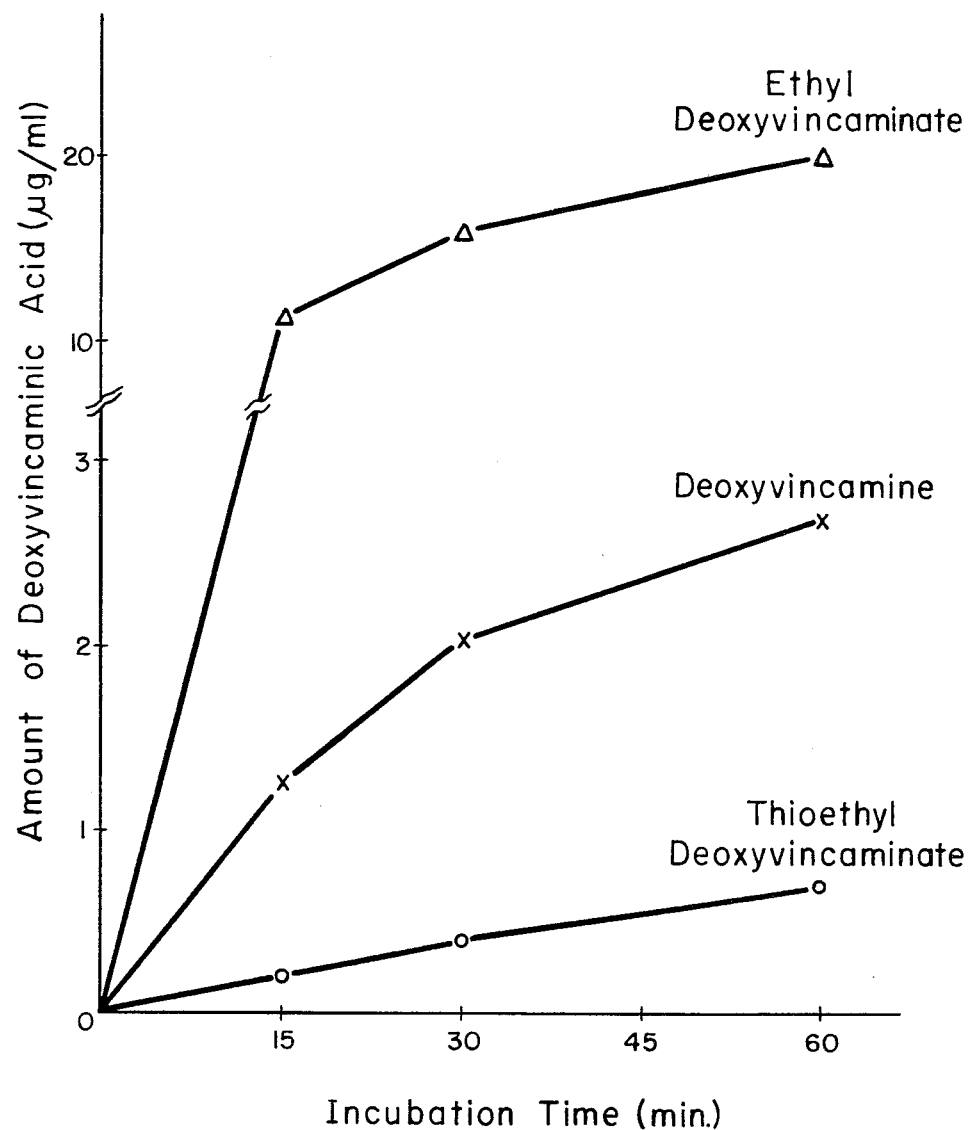
FIG. 2 is a graph showing relative rates of hydrolysis of the thioethyl deoxyvincaminate compound of the present invention and comparative compounds using guinea pig lever homogenate.

Rates of hydrolysis of the compounds of the present invention and the comparative compounds were determined using guinea pig liver homogenate solution. Test compounds were added to a 0.5% homogenate solution to obtain a final concentration of 25 μg/ml and incubated at 30° C. At various intervals of incubation, the amount of product obtained through hydrolysis, ie. vincaminic acid or deoxyvincaminic acid, was measured. The results are shown in FIG. 1 and FIG. 2.

As demonstrated by the results of the above, the compounds according to the present invention have similar or superior extending effects on survival time when compared with vincamine or corresponding alcohol esters of vincaminic acid and are hardly hydrolyzed by liver esterase. Therefore, these compounds are useful as long acting cerebral metabolic and circulatory regulators for the treatment of various diseases caused by cerebral blood flow disorders and/or depression of oxygenation in the brain, for example, cerebral apoplexy (cerebral hemorrhage, cerebral thrombosis, cerebral embolism), cerebral arteriosclerosis, hypertensive disturbance of cerebral circulation, post traumatic cerebral symptoms, memory defects, headache, deafness, tinnitus, vertigo, Meniere disease, retinopathy, etc. Advantageously, lower dosages or less frequent administrations may be possible than with the known compounds.

For use as medicines, the compounds of the present invention can be prepared in combination with suitable medical carriers or diluents, and can be prescribed by conventional methods in oral or non-oral dosage forms.

In prescriptions, the compounds of the present invention can be used in the form of the pharmacologically acceptable salts thereof. The compounds may be used singly or in an appropriate combination with other pharmaceutically active components.

For oral administration, the compounds can be prepared as tablets, pills, capsules, powders granules and the like using at least one excipient such as starch, lactose, sucrose, mannitol, carboxymethylcellulose. This pharmaceutical preparation may also contain lubricants, for example, magnesium stearate, sodium lauryl sulfate and talc, binders, for example, dextrin, crystalline cellulose, polyvinylpyrrolidone, acacia gum, corn starch and gelatine, and disintegrators, for example, potato starch and carboxymethylcellulose, if needed. Further, the compounds can be administered in any form of suspensions, emulsions, syrups and elixirs, which may contain flavor or coloring agents.

As non-oral preparations, the compounds can be prescribed as sterile, aqueous or non-aqueous, injectable solutions or injectable suspensions. As diluents, the following may generally be used to prepare injectable solutions: distilled water, physiological saline solution, aqueous solution of dextrose, vegetable oil, propylene glycol, polyethylene glycol and the like. Isotonizing agents, solubilizers, stabilizers antiseptics and/or pain removing agents may be also contained in this preparation, if necessary. Further, this type of preparation can be made in the form of a sterilized solid composition which is to be dissolved in sterilized water or other sterilized medium for injection at use.

As other non-oral preparations, suppositories can be prepared by mixing the compound with suitable bases.

The desired dosage of the compound of the present invention is variable according to subject, route of administration, period of treatment and so on. Generally, for an adult, administration of 1-500 mg per day may be preferable to obtain the desired treatment effect, and, for example, a preparation containing 1-100 mg of the compound of the present invention can be administered in dosages of one to several units per day.

Examples of prescription pharmaceuticals containing the compounds of this invention as active ingredients are described below. These examples are illustrative only and are non-limiting in scope.

PRESCRIPTION EXAMPLE 1

(tablet containing 25 mg of the invention compound)

| Component | Amount per tablet (mg) |
|---|---|
| the invention compound | 25 |
| lactose | 120 |
| corn starch | 50 |
| magnesium stearate | 5 |
| | total 200 mg |

The invention compound, lactose and corn starch are equally mixed, kneaded together with water and shaped into granules by a granulating machine. After drying by warm air, the granules are mixed with magnesium stearate and shaped into tablets by a tablet machine.

PRESCRIPTION EXAMPLE 2

(capsule containing 30 mg of the invention compound)

| Component | Amount per capsule (mg) |
|---|---|
| the invention compound | 30 |
| lactose | 120 |
| | total 150 mg |

The above components are equally mixed and charged in hard capsules.

PRESCRIPTION EXAMPLE 3

(injection of 3 ml containing 15 mg of the invention compound)

| Component | Amount in 3 ml (mg) |
|---|---|
| the invention compound | 15 |
| sodium chloride | proper amount |
| distilled water for injection | proper amount |
| | total 3 ml |

The above components are mixed to form a uniform solution. The solution is filtered and charged in 3 ml ampoule. The ampoule is closed by fusion followed by sterilizing.

PRESCRIPTION EXAMPLE 4

(suppository containing 50 mg of the invention compound)

| Component | Amount per one unit (mg) |
|---|---|
| the invention compound | 50 |
| cocoa butter | 1950 |
| | total 2000 mg |

The invention compound is added into the melted base and mixed thoroughly. Stirring is continued until shaping is achieved.

What is claimed is:

1. Compounds having the general formula (I):

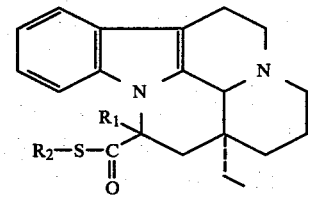

wherein $R_1$ is hydrogen or a hydroxyl group and $R_2$ is an alkyl group having 1 to 4 carbon atoms, and salts thereof.

2. Pharmacologically acceptable salts of the compounds according to claim 1.

3. A compound according to claim 1 comprising vincaminic acid thioethyl ester.

4. A compound according to claim 1 comprising deoxyvincaminic acid thioethyl ester.

5. Cerebral metabolic and circulatory regulators in which the active ingredient comprises a compound having the general formula (I):

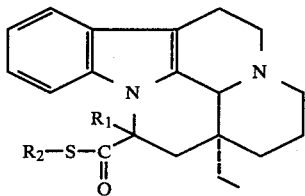

wherein $R_1$ is hydrogen or a hydroxyl group and $R_2$ is an alkyl group having 1 to 4 carbon atoms, or a pharmacologically acceptable salt thereof.

6. Cerebral metabolic and circulatory regulators in which the active ingredient comprises a pharmacologically acceptable salt of a compound having the general formula (I):

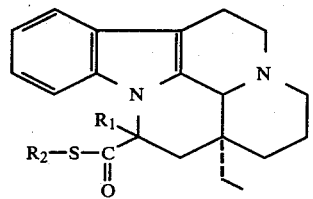

wherein $R_1$ is hydrogen or a hydroxyl group and $R_2$ is an alkyl group having 1 to 4 carbon atoms.

7. Cerebral metabolic and circulatory regulators according to one of claims 5 or 6, wherein the active ingredient is vincaminic acid thioethyl ester or a pharmacologically acceptable salt of vincaminic acid thioethyl ester.

8. Cerebral metabolic and circulatory regulators according to one of claims 5 or 6, wherein the active ingredient is deoxyvincaminic acid thioethyl ester or a pharmacologically acceptable salt of deoxyvincaminic acid thioethyl ester.

9. A method for treating cerebral blood flow disorders which comprises administering to a host a therapeutically effective dose of a compound having the general formula (I):

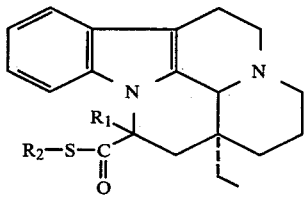

wherein $R_1$ is hydrogen or a hydroxyl group and $R_2$ is an alkyl group having 1 to 4 carbon atoms, or a pharmacologically acceptable salt thereof.

* * * * *

UNITED STATES PATENT AND TRADEMARK OFFICE
CERTIFICATE OF CORRECTION

PATENT NO. : 4,364,947
DATED : December 21, 1982
INVENTOR(S) : Yoshio Toyomaki

It is certified that error appears in the above—identified patent and that said Letters Patent is hereby corrected as shown below:

Insert in Column 3, line 49 following 1685 $cm^{-1}$, --Elemental analysis ($C_{22}H_{28}N_2O_2S$ = 384.54);--.

Insert in Column 4, line 7 following 1675 $cm^{-1}$, --Elemental analysis ($C_{22}H_{28}N_2O_2S$ = 368.55);--.

Column 5, line 23, "capsules, powders granules" should be --capsules, powders, granules--.

Signed and Sealed this

Twenty-first Day of June 1983

[SEAL]

Attest:

DONALD J. QUIGG

Attesting Officer

Acting Commissioner of Patents and Trademarks